United States Patent
Nandi et al.

(10) Patent No.: US 10,639,619 B2
(45) Date of Patent: May 5, 2020

(54) ALKYLATION CATALYST

(71) Applicant: ExxonMobil Research and Engineering Company, Annandale, NJ (US)

(72) Inventors: Partha Nandi, Annandale, NJ (US); Matthew S. Ide, Doylestown, PA (US); Jihad M. Dakka, Whitehouse Station, NJ (US); Quddus A. Nizami, Spring, TX (US); Mobae Afeworki, Phillipsburg, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 16/018,202

(22) Filed: Jun. 26, 2018

(65) Prior Publication Data

US 2019/0022631 A1 Jan. 24, 2019

Related U.S. Application Data

(60) Provisional application No. 62/534,378, filed on Jul. 19, 2017.

(51) Int. Cl.
| | | |
|---|---|---|
| *B01J 29/06* | (2006.01) | |
| *B01J 29/70* | (2006.01) | |
| *C10G 29/20* | (2006.01) | |
| *C07C 2/66* | (2006.01) | |
| *C10G 29/12* | (2006.01) | |
| *B01J 37/02* | (2006.01) | |
| *B01J 37/00* | (2006.01) | |
| *B01J 37/08* | (2006.01) | |
| *B01J 37/26* | (2006.01) | |
| *C07C 2/12* | (2006.01) | |
| *C07C 2/68* | (2006.01) | |

(52) U.S. Cl.
CPC ....... *B01J 29/7088* (2013.01); *B01J 29/7038* (2013.01); *B01J 37/0009* (2013.01); *B01J 37/0201* (2013.01); *B01J 37/023* (2013.01); *B01J 37/08* (2013.01); *B01J 37/26* (2013.01); *C07C 2/12* (2013.01); *C07C 2/66* (2013.01); *C07C 2/68* (2013.01); *C10G 29/12* (2013.01); *C10G 29/205* (2013.01); *B01J 2229/18* (2013.01); *B01J 2229/183* (2013.01); *B01J 2229/186* (2013.01); *B01J 2229/20* (2013.01); *B01J 2229/42* (2013.01); *C07C 2529/70* (2013.01)

(58) Field of Classification Search
CPC ................ B01J 29/7038; B01J 29/7088; B01J 35/0009; B01J 37/26; B01J 37/08; B01J 37/0201; B01J 37/023; B01J 2229/20; B01J 2229/42; B01J 2229/18; B01J 2229/183; B01J 2229/186; C07C 2529/70
USPC .................................. 502/60, 63, 64, 69, 85
See application file for complete search history.

(56) References Cited

U.S. PATENT DOCUMENTS

| | | | |
|---|---|---|---|
| 4,278,827 A | 7/1981 | Chu et al. | |
| 6,358,400 B1* | 3/2002 | Bogdan ................ | C10G 35/065 208/133 |
| 8,211,822 B2* | 7/2012 | Mueller ............... | C07D 301/12 502/242 |
| 2006/0224030 A1 | 10/2006 | Euzen et al. | |
| 2007/0043226 A1* | 2/2007 | Muller ................. | C07D 301/12 549/529 |
| 2012/0083636 A1 | 4/2012 | Boldingh | |
| 2016/0256859 A1 | 9/2016 | Parvulescu et al. | |

OTHER PUBLICATIONS

Corma et al., "Delaminated zeolite precursors as selective acidic catalysts", Nature, 1998, vol. 396, pp. 353-356.
The International Search Report and Written Opinion of PCT/US2018/039396 dated Oct. 15, 2018.
Araya et al., "Mobility of salt molecules in zeolites", Zeolites, 1, (1981), 35-40.

* cited by examiner

Primary Examiner — Elizabeth D Wood
(74) Attorney, Agent, or Firm — Andrew T. Ward; Ryan L. Lobato (57) ABSTRACT

Catalyst compositions with improved alkylation activity and corresponding methods for making such catalyst compositions are provided. The catalyst(s) correspond to solid acid catalysts formed by exposing a catalyst precursor with a zeolitic framework structure to a molten metal salt that includes fluorine, such as a molten metal fluoride. The resulting fluorinated solid acid catalysts can have improved alkylation activity while having a reduced or minimized amount of structural change due to the exposure to the molten metal fluoride. This is in contrast to fluorinated solid acid catalysts that are exposed to higher severity forms of fluorination, such as exposure to ammonium fluoride or HF. $SnF_2$ is an example of a suitable molten metal fluoride.

5 Claims, 3 Drawing Sheets

ALKYLATION CATALYST

CROSS-REFERENCE TO RELATED APPLICATIONS

This application claims priority to U.S. Provisional Application 62/534,378 filed Jul. 19, 2017, which is herein incorporated by reference in its entirety.

FIELD

Methods and catalyst compositions are provided for alkylation of aromatic compounds.

BACKGROUND

Alkylation processes typically require a solid acid catalyst or a liquid-based acid catalyst. Typically, solid acid catalysts are based on strong Bronstead acid sites. Liquid phase to alkylation catalysts typically correspond to $H_2SO_4$, HF, or ionic liquids that have fluoride-based counter anions. Liquid phase alkylation catalysts can tend to pose a variety of challenges in a refinery setting, due in part to the corrosive nature of the liquids. Solid acid catalysts tend to pose fewer difficulties with regard to handling, but also tend to lack activity comparable to the liquid phase catalysts, particularly at lower temperatures.

What is needed is a solid-acid catalyst composition with improved alkylation activity that can be formed while reducing or minimizing handling of corrosive substances.

A journal article by Corma et al. (Nature, Vol. 396, pg 353, 1998) describes delamination of zeolite precursors, such as MCM-22 precursors, by treating the zeolite precursors with basic solutions. The treatment results in alteration of the crystalline structure, leading to a reduction in long-range order and an increase in surface area.

SUMMARY

In an aspect, a catalyst composition comprising an MWW framework structure is provided. The catalyst composition can include 0.1 wt % to 2.5 wt % fluorine relative to a weight of the catalyst composition. Additionally or alternately, the catalyst composition and/or the MWW framework structure can include a weight ratio of Sn to F of 2.0 or less, such as 0.1 to 2.0. Additionally or alternately, at least one of the MWW framework structure and the catalyst composition can include 2.5 wt % or less Sn, such as 0.01 wt % to 2.5 wt % Sn. Examples of an MWW framework structure include MCM-49, MCM-22, MCM-56, or a combination thereof. Optionally, the catalyst composition can further include a binder.

Such a catalyst composition can be formed by exposing a catalyst precursor comprising a zeolitic framework structure to a molten metal salt comprising fluoride anion at a temperature of 275° C. or less. The catalyst precursor and the molten metal salt can then be mixed during at least a portion of the exposing to form a catalyst comprising a fluorinated zeolitic framework structure. In addition to catalysts/catalyst precursors having an MWW framework structure, other suitable zeolitic framework structures can include a FAU framework structure, a MOR framework structure, a MEI framework structure, a MFS framework structure, a *BEA framework structure, a EMT-FAU structural intermediate framework structure, or a combination thereof. The molten metal salt can correspond to $SnF_2$, a molten metal fluoride, or another convenient metal salt that includes fluoride anion.

Optionally, after fluorination of the zeolitic framework structure, the catalyst can be used to form a catalyst composition, such as by extrusion and/or combination with other materials, such as one or more binders. Optionally, a surface area of such a catalyst composition can be different from a surface area of a catalyst precursor composition formed under substantially similar extruding and calcining conditions by 25% or less relative to the surface area of the catalyst precursor composition.

A catalyst composition can be used for performing alkylation. For example, a feedstock can be exposed to a catalyst composition as described above under effective alkylation conditions to form an alkylated effluent composition. Optionally, the feedstock can include olefinic hydrocarbons and 1-ring aromatic hydrocarbons (such as benzene). Optionally, the effective alkylation conditions can include effective transalkylation conditions.

DETAILED DESCRIPTION

Overview

In various aspects, catalyst compositions with improved alkylation activity and corresponding methods for making such catalyst compositions are provided. The catalyst(s) correspond to solid acid catalysts formed by exposing a catalyst precursor with a zeolitic framework structure to a molten metal fluoride and/or a molten metal salt that includes fluorine (i.e., in the form of a fluoride anion). The resulting fluorinated solid acid catalysts can have improved alkylation activity while having a reduced or minimized amount of structural change due to the exposure to the molten metal fluoride. This is in contrast to fluorinated solid acid catalysts that are exposed to higher severity forms of fluorination, such as exposure to ammonium fluoride or HF. $SnF_2$ is an example of a suitable molten metal fluoride. Other examples of potentially suitable molten fluorides can include $TaF_5$ and/or other metal fluorides that have a melting point of 275° C. or less.

Alkylation processes generally correspond to processes where an olefin is reacted with an aromatic compound to form an alkylated product (i.e., a product that includes the carbons in the olefin as a new side chain attached to the aromatic.) Due to the lower alkylation activity of typical solid acid catalysts, various techniques have been used to try to improve the activity.

A common method for modifying the activity of a zeolitic catalyst is to fluorinate the catalyst. Adding fluorine to a zeolitic catalyst can increase the acidity of a catalyst, which can often enhance the activity. However, conventional methods of adding fluorine to a zeolitic catalyst can also tend to alter the structure. For some fluorination methods, this can be due in part to the basic environment that is often created, such as when ammonium fluoride is used as the fluorination agent. For example, as explained in the Corma et al. journal article noted above, exposing a precursor structure for MCM-22 to a suitable basic environment can result in delamination of the structure, so that an alternative structure is formed.

In contrast to conventional methods, it has been unexpectedly discovered that molten metal fluoride (and/or other molten metal salts that contain a fluoride anion) can be used to add fluorine to a crystals having a zeolitic framework structure. A suitable metal fluoride can correspond to $SnF_2$, which has a melting point of 208° C. $TaF_5$ (tantalum fluoride) also has a melting point of roughly 206° C., and therefore may also be suitable for forming a molten metal fluoride to add fluorine to a zeolitic framework structure. In some optional aspects, still other materials that may be suitable for fluorination can include molten metal hydroxyfluorides or molten metal halidefluorides (i.e., including both fluorine and another halogen).

The relatively low melting point of $SnF_2$ can allow crystals having/including a zeolitic framework structure (a catalyst precursor) to be exposed to the $SnF_2$ in a molten state at a temperature of 275° C. or less, or 250° C. or less, or 225° C. or less. Under these low severity conditions, the crystals of the zeolitic framework structure can be exposed to an appropriate amount of molten $SnF_2$ so that a target amount of fluorine is incorporated into the zeolitic framework structure. During this exposure, the crystals having the zeolitic framework structure can be mixed with the molten $SnF_2$. This can be accomplished, for example, by exposing the crystals having the zeolitic framework structure to the molten $SnF_2$ in a rotatable drum. The crystals and molten $SnF_2$ can then be mixed together by rotation of the drum. Any convenient rotational speed can be used, such as a rotational speed of ~5 revolutions per minute (rpm) or greater. Additionally or alternately, any other convenient method of mixing the crystals having the zeolitic framework structure with the molten $SnF_2$ can be used.

In various aspects, exposing crystals that have/include a zeolitic framework structure to a molten metal fluoride can have a reduced or minimized impact on the zeolitic framework structure. In particular, crystals having a fluorinated zeolitic framework structure that is produced by exposure of crystals to a molten metal fluoride can have a similar or comparable X-ray diffraction pattern relative to the crystals of the zeolitic framework structure prior to fluorination. Additionally or alternately, the total surface area for catalyst compositions of the fluorinated zeolitic framework structure (such as catalyst compositions corresponding to bound extrudates of the catalyst) can differ from the total surface area for comparable catalyst precursor compositions by only a modest amount, such as a difference of 25% or less relative to a surface area of the catalyst precursor composition, or 20% or less, or 15% or less. For such a total surface area comparison, the catalyst precursor composition can be formed by extruding and calcining the catalyst precursor composition under conditions that are substantially similar to the conditions used for extruding and calcining of the catalyst composition. The comparable extruding and calcining conditions can also include incorporation of a substantially similar binder for both the catalyst precursor composition and the catalyst composition.

In various aspects, using molten metal fluoride (and/or another suitable molten metal salt corresponding to a fluorine source) to fluorinate a zeolitic framework structure can result in incorporation of an unexpectedly low amount of the metal from the metal fluoride into the framework structure. As an example, $SnF_2$ has a molecular weight of roughly 157 g/mole, which corresponds to roughly 38 g/mole of fluorine and roughly 119 g/mole of tin. Based on this weight disparity, it could be expected that exposure of a zeolitic framework structure to molten $SnF_2$ would result in incorporation of a substantially larger weight of tin into the framework structure as compared with fluorine. However, it has been discovered that the weight of tin added to the zeolitic framework structure is comparable to or less than the weight of fluorine added. Instead of incorporating into the zeolitic framework structure, it has been discovered that a substantial portion of the tin instead forms tin oxide as a separate phase. This separate tin oxide phase can be separated from the catalyst particles that are formed by extrusion. Based on the substantially lower atomic weight of fluorine relative to tin (~19 g/mole versus 119 g/mole), this means that the molar amount of tin incorporated into the zeolitic framework structure is substantially lower than the molar amount of fluorine.

In this discussion, a zeolitic framework structure prior to exposure to a molten metal salt suitable as a fluorine source can be referred to as a catalyst precursor. The resulting fluorinated zeolitic framework structure can be referred to as a catalyst. A catalyst precursor and/or a catalyst can optionally be combined with other materials typically found in a catalyst precursor or catalyst, such as a binder. In various aspects, a catalyst precursor can be converted into a catalyst by exposure of catalyst precursor crystals to molten metal fluoride. The resulting catalyst can then be extruded (optionally after combination with a binder) to form catalyst particles corresponding to a catalyst composition. In this discussion, a catalyst composition can correspond to a catalyst itself (i.e., catalyst crystals, optionally after extrusion) or to a catalyst formulated with/combined with/extruded with one or more additional materials (such as a binder and/or other catalytic materials).

In this discussion, a zeolite is defined to refer to a crystalline material having a porous framework structure built from tetrahedra atoms connected by bridging oxygen atoms. Examples of known zeolite frameworks are given in the "Atlas of Zeolite Frameworks" published on behalf of the Structure Commission of the International Zeolite Association", $6^{th}$ revised edition, Ch. Baerlocher, L. B. McCusker, D. H. Olson, eds., Elsevier, New York (2007) and the corresponding web site, www.iza-structure.org. Under this definition, a zeolite can refer to aluminosilicates having a zeolitic framework type as well as crystalline structures containing oxides of heteroatoms different from silicon and aluminum. Such heteroatoms can include any heteroatom generally known to be suitable for inclusion in a zeolitic framework, such as gallium, boron, germanium, phosphorus, zinc, and/or other transition metals that can substitute for silicon and/or aluminum in a zeolitic framework.

Weight of molecular sieve, weight of binder, weight of catalyst composition, weight ratio of molecular sieve over catalyst composition, and weight ratio of binder over catalyst composition are calculated based on calcined weight (at 510° C. in air for 24 hours), i.e., the weight of the molecular sieve, the binder, and the catalyst composition are calculated based on the weight of the molecular sieve, the binder, and the catalyst composition after being calcined at 510° C. in air for twenty-four hours.

The term "aromatic" as used herein is to be understood in accordance with its art-recognized scope which includes alkyl substituted and unsubstituted mono- and polynuclear compounds.

Solid Acid Catalyst

Solid acid catalysts can generally refer to solid materials that can provide acidic sites for catalysis of reactions. Some examples of solid acid catalysts can include various types of zeolites and/or molecular sieves. For example, in zeolitic structures that include silicon and aluminum in the framework, the aluminum atoms can potentially serve as acidic catalysis sites. Suitable zeolitic materials for use as solid acid catalysts can include ZSM-4 (framework type MAZ), ZSM-20 (EMT-FAU structural intermediate), ZSM-3 (EMT-FAU structural intermediate), ZSM-18 (MEI), zeolite Beta (*BEA), faujasite (FAU), mordenite (MOR), zeolite Y (FAU), ZSM-57 (MFS), and rare earth metal-containing forms thereof. More generally, crystalline materials having a porous framework structure built from tetrahedra atoms connected by bridging oxygen atoms can potentially be suitable solid acid catalysts. This can include aluminosilicates having a zeolitic framework as well as crystalline zeolitic framework structures containing oxides of heteroatoms different from silicon and aluminum. Such heteroatoms can include any heteroatom generally known to be suitable for inclusion in a zeolitic framework, such as gallium, boron, germanium, phosphorus, zinc, and/or other transition metals that can substitute for silicon and/or aluminum in a zeolitic framework In some aspects, an alkylation catalyst composition can include a solid acid catalyst having the MWW framework structure. Examples of molecular sieves having an MWW framework structure include MCM-22, MCM-49, MCM-56, MCM-36, EMM-10, EMM-13, ITQ-1, ITQ-2, UZM-8, MIT-1, and interlayer expanded zeolites.

Crystalline microporous materials of the MWW framework type include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

A zeolitic framework structure can optionally be characterized based on having a composition with a molar ratio $YO_2$ over $X_2O_3$=n, wherein X is a trivalent element, such as aluminum, boron, iron, indium and/or gallium, preferably aluminum and/or gallium, and Y is a tetravalent element, such as silicon, tin and/or germanium, preferably silicon. For a MWW framework structure, n can be less than about 50, e.g. from about 2 to about 50, usually from about 10 to about 50, more usually from about 15 to about 40. Optionally, the above n values can correspond to n values for a ratio of silica to alumina in the MWW framework structure. In such optional aspects, the molecular sieve can optionally correspond to an aluminosilicate and/or a zeolite.

Optionally, a catalyst composition can include 0.01 wt % to 5.0 wt %, or 0.01 wt % to 2.0 wt %, or 0.01 wt % to 1.0 wt %, or 0.05 wt % to 5.0 wt %, or 0.05 wt % to 2.0 wt %, or 0.05 wt % to 1.0 wt %, or 0.1 wt % to 5.0 wt %, or 0.1 to 2.0 wt. %, or 0.1 wt % to 1.0 wt %, of a metal element of Groups 6-11 (according to the IUPAC Periodic Table). The metal element may be at least one hydrogenation component, such as tungsten, vanadium, molybdenum, rhenium, chromium, manganese, one or more metals selected from Groups 8-10 of the Periodic Table of the Elements, or mixtures thereof. Optionally, the metal can be a Group 8-10 noble metal. Specific examples of useful metals are iron, ruthenium, osmium, nickel, cobalt, rhodium, iridium, copper, tin and noble metals such as platinum or palladium. Specific examples of useful bimetallic combinations are bimetallics where Pt is one of the metals, such as Pt/Sn, Pt/Pd, Pt/Cu, and Pt/Rh. In some aspects, the metal component is palladium, platinum, rhodium, copper, tin, or a combination thereof. The amount of the metal component can be selected according to a balance between hydrogenation activity and catalytic functionality. For a metal component including two or more metals (such as a bimetallic hydrogenation component), the ratio of a first metal to a second metal can range from 1:1 to 1:10. If an optional metal component is supported on the catalyst composition, the optional metal component can be incorporated into the catalyst composition by any convenient method.

Optionally, an alkylation catalyst composition including an MWW framework molecular sieve can further include one or more additional molecular sieves. Examples of additional suitable molecular sieves can include, but are not limited to, molecular sieves with a framework structure having a 3-dimensional network of 12-member ring pore channels. Examples of framework structures having a 3-dimensional 12-member ring are the framework structures corresponding to faujasite (such as zeolite X or Y, including USY), *BEA (such as zeolite Beta), BEC (polymorph C of Beta) CIT-1 (CON), MCM-68 (MSE), hexagonal faujasite (EMT), ITQ-7 (ISV), ITQ-24 (IWR), and ITQ-27 (IWV), preferably faujasite, hexagonal faujasite, and Beta (including all polymorphs of Beta).

For a molecular sieve having the framework structure of Beta and/or its polymorphs, n can be about 10 to about 60, or about 10 to about 50, or about 10 to about 40, or about 20 to about 60, or about 20 to about 50, or about 20 to about 40, or about 60 to about 250, or about 80 to about 250, or about 80 to about 220, or about 10 to about 400, or about 10 to about 250, or about 60 to about 400, or about 80 to about 400. For a molecular sieve having the framework structure FAU, n can be about 2 to about 400, or about 2 to about 100, or about 2 to about 80, or about 5 to about 400, or about 5 to about 100, or about 5 to about 80, or about 10 to about 400, or about 10 to about 100, or about 10 to about 80.

In some aspects, an MWW framework type material may be contaminated with other crystalline materials, such as ferrierite or quartz. These contaminants may be present in quantities of less than about 10% by weight, normally less than about 5% by weight.

Although it may be possible to form self-bound catalyst particles composed primarily of extruded crystals of a zeolitic material, in various aspects it can be desirable to incorporate other materials in a catalyst composition, such as materials that are resistant to the temperatures and other conditions employed in an alkylation process. Such materials include active and inactive materials and synthetic or naturally occurring zeolites, as well as inorganic materials such as clays, silica, hydrotalcites, perovskites, spinels, inverse spinels, mixed metal oxides, and/or metal oxides such as alumina, lanthanum oxide, cerium oxide, zirconium oxide, and titania. The inorganic material may be either naturally occurring, or in the form of gelatinous precipitates or gels including mixtures of silica and metal oxides.

Use of a material in conjunction with a zeolitic material, i.e. combined therewith or present during its synthesis, which itself is catalytically active, may change the conversion and/or selectivity of the catalyst composition. Inactive materials suitably serve as diluents to control the amount of conversion so that transalkylated products can be obtained in an economical and orderly manner without employing other means for controlling the rate of reaction. These catalytically active or inactive materials may be incorporated into, for example, alumina, to improve the crush strength of the catalyst composition under commercial operating conditions. It is desirable to provide a catalyst composition having good crush strength because in commercial use, it is desirable to prevent the catalyst composition from breaking down into powder-like materials.

Naturally occurring clays that can be composited with each molecular sieve as a binder for the catalyst composition include the montmorillonite and kaolin family, which families include the subbentonites, and the kaolins commonly known as Dixie, McNamee, Ga. and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, an MWW framework material can be composited with a binder or matrix material, such as an inorganic oxide selected from the group consisting of silica, alumina, zirconia, titania, thoria, beryllia, magnesia, lanthanum oxide, cerium oxide, manganese oxide, yttrium oxide, calcium oxide, hydrotalcites, perovskites, spinels, inverse spinels, and combinations thereof, such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. It may also be advantageous to provide at least a part of the foregoing porous matrix binder material in colloidal form so as to facilitate extrusion of the catalyst composition.

The relative proportions of zeolitic material and inorganic oxide binder may vary widely. For example, the amount of binder employed may be as little as 0 wt %, or alternatively at least 1 wt %, or at least 5 wt %, or at least 10 wt %, whereas in other embodiments the catalyst may include up to 90 wt %, for example up 80 wt %, such as up to 70 wt %, for example up to 60 wt %, such as up to 50 wt % of a binder material.

In some aspects, a catalyst composition including a solid acid catalyst can be substantially free of any binder containing amorphous alumina. As used herein, the term "substantially free of any binder containing amorphous alumina" means that the solid acid catalyst used herein contains less than 5 wt %, such as less than 1 wt %, and preferably no measurable amount, of amorphous alumina as a binder. Surprisingly, it is found that when the solid acid catalyst is substantially free of any binder containing amorphous alumina, the activity of the catalyst for isoparaffin-olefin alkylation can be significantly increased, for example by at least 50%, such as at least 75%, even at least 100% as compared with the activity of an identical catalyst but with an amorphous alumina binder.

The particle size and the nature of the alkylation catalyst composition can usually be determined by the type of alkylation process which is being carried out, such as: a down-flow, liquid phase, fixed bed process; an up-flow, fixed bed, liquid phase process; an ebullating, fixed fluidized bed liquid or gas phase process; or a liquid or gas phase, transport, fluidized bed process, as noted above, with the fixed-bed type of operation preferred.

Prior to use, steam treatment of the catalyst composition may be employed to minimize the aromatic hydrogenation activity of the catalyst composition. In the steaming process, the catalyst composition is usually contacted with from 5 to 100% steam, at a temperature of at least 260° to 650° C. for at least one hour, specifically 1 to 20 hours, at a pressure of 100 to 2590 kPa-a.

A catalyst composition (and/or crystals of a catalyst or catalyst precursor) can be dried by heating at a temperature of 65° C. to 160° C., typically 110° C. to 143° C., for at least 1 minute and generally not longer than 24 hours, at pressures ranging from 100 to 200 kPa-a. Thereafter the catalyst composition may be calcined in a stream of dry gas, such as air or nitrogen, at temperatures of from 260° C. to 650° C. for 1 to 20 hours. Calcination is typically conducted at pressures ranging from 100 to 300 kPa-a.

Alkylation Feedstock and Process

For aromatic alkylation, suitable feedstocks for alkylation can include feedstocks containing 1-ring aromatics and/or multi-ring aromatics. For example, a feedstock can include about 5.0 wt % or more of 1-ring (mononuclear) aromatics, or about 10 wt % or more, or about 20 wt % or more, such as up to 50 wt % or possibly still higher. Additionally or alternately, a feedstock for alkylation can include about 1.0 wt % or more of polynuclear aromatics, or about 2.0 wt % or more, or about 5.0 wt % or more, or about 10.0 wt % or more, such as up to 50 wt % or possibly still higher. Additionally or alternately, the feedstock can include about 1.0 wt % or more of alkylated mononuclear aromatics, or about 2.0 wt % or more, or about 5.0 wt % or more, or about 10 wt % or more, such as up to 50 wt % or still higher. Examples of suitable aromatics can include, but are not limited to, benzene, naphthalene, toluene, xylene, ethylbenzene, and combinations thereof.

In addition to aromatics, a feedstock for an alkylation process can also include olefins. Examples of suitable olefins can include, but are not limited to, propene, 1-butene, and 2-butene. More generally, any convenient type of aliphatic olefin may be used if larger alkylation products are desired. Other examples of olefins include bio-based sources of olefins, such as unsaturated fatty acids.

The feedstock weight percentages provided herein correspond to a combined feed that includes both olefins and the aromatics for alkylation. However it is understood that various portions of a feedstock can be separately introduced into an alkylation reaction zone that contains the alkylation catalyst described herein.

For alkylation of aromatics, an alkylation process can be conducted at a temperature of about 400° C. or less, or about 360° C. or less, or about 320° C. or less, and/or at least about 100° C., or at least about 200° C., such as between 100° C. to 400° C., or 100° C. to 340° C., or 230° C. to 300° C.; a pressure of 2.0 MPag to 10.0 MPag, or 3.0 MPag to 8.0 MPag, or 3.5 MPag to 6.0 MPag; an $H_2$:hydrocarbon molar ratio of 0 to 20, or 0.01 to 20, or 0.1 to 10; and a weight hourly space velocity ("WHSV") for total hydrocarbon feed to the reactor(s) of 0.1 to 100 $hr^{-1}$, or 1 to 20 $hr^{-1}$. Optionally, the pressure during an alkylation process corresponding to transalkylation can be at least 4.0 MPag. Some of the conditions correspond to gas phase alkylation conditions, while other conditions can include at least a portion of a liquid phase. For gas phase alkylation, the alkylation can be performed in any convenient type of gas phase reactor, such as a riser reactor. For alkylation performed at least in part in the liquid phase, the feed can be exposed to the alkylation catalyst under fixed bed conditions, fluidized bed conditions, or other conditions that are suitable when a substantial liquid phase is present in the reaction environment.

EXAMPLES

Crystals of MCM-49 were synthesized using a conventional synthesis method. The MCM-49 crystals showed the expected X-ray diffraction pattern. Some of the crystals were calcined in a box furnace at 200° C. for 16 hours. These calcined MCM-49 crystals are referred to in this Example as Catalyst 1.

The MCM-49 crystals were also used as catalyst precursors for production of fluorinated MCM-49 catalysts with varying amounts of fluorine content. The fluorinated MCM-49 catalysts were produced by exposing the MCM-49 crystals (catalyst precursor) to molten $SnF_2$.

Most of the fluorinated MCM-49 crystals in this Example (Catalysts 3-7) were prepared in the following manner. 20 grams of MCM-49 crystals (not calcined) were placed in a 125 ml polytetrafluoroethylene liner. An amount of $SnF_2$ was added to correspond to the desired weight of fluorine in the resulting fluorinated crystals. The $SnF_2$ corresponded to 99 wt % pure tin(II) fluoride from Sigma Aldrich. The liner was then assembled in an autoclave with a rupture disk. The autoclave was then assembled and tightened into a rotational oven to allow for rotation during heating, such as at a rotation speed of 5 rpm or greater. The autoclave was then rotated while maintaining the oven at 250° C. for 16 hours.

The amount of $SnF_2$ added to the liner varied depending on the desired fluorine concentration in the final crystals. For a fluorine concentration of 2.0 wt % in the fluorinated crystals (Catalyst 3), 2.5 grams of the tin(II) fluoride was added. For a fluorine concentration of 1.6 wt % in the fluorinated crystals (Catalyst 4), 2.0 grams of the tin(II) fluoride was added. For a fluorine concentration of 1.2 wt % in the fluorinated crystals (Catalyst 5), 1.2 grams of the tin(II) fluoride was added. For a fluorine concentration of 0.8 wt % in the fluorinated crystals (Catalyst 6), 1.0 grams of the tin(II) fluoride was added. For a fluorine concentration of 0.4 wt % in the fluorinated crystals (Catalyst 7), 0.5 grams of the tin(II) fluoride was added.

An additional catalyst (Catalyst 2) was prepared with a target fluorine content of 2.0 wt % but without use of the rotational oven. For Catalyst 2, 20 grams of MCM-49 crystals (not calcined) and 2.5 grams of tin(II) fluoride were placed in a liner. The liner was assembled in an autoclave with a rupture disk. The autoclave was then placed in a static oven. The oven was maintained at a temperature of 250° C. for 16 hours.

After forming Catalysts 1-7, the catalyst was cooled prior to extrusion to form catalyst particles. The cooled catalyst crystals were mixed with a silica binder and extruded to form silica-bound catalyst particles. The resulting catalyst particles were then used to catalyze a reaction between benzene and propene. Laboratory scale amounts of the silica-bound extruded catalyst particles from Catalysts 1-7 were mixed with benzene and propene in a reactor.

Relative catalyst activity and selectivity for aromatic alkylation was determined for each of the catalyst compositions of Examples 1 to 3 based on a cumene alkylation test. The cumene alkylation test corresponded to loading the samples of the dried silica-bound extruded catalyst compositions into a batch reactor along with benzene. The reactor was then heated to 266° F. (130° C.) followed by the addition of propylene under an inert gas pressure of 300 psig (~2.1 MPag). Samples were removed periodically for the duration of the test and analyzed with gas chromatography to determine the activity and selectivity of benzene alkylation with propylene. The catalytic activity of the catalyst was evaluated by monitoring the conversion of benzene and propylene as a function of time and determining a rate constant, k, which was $10^3$ times the rate constant in units of $cm^3/g*mol*hr$. The selectivity to di-isopropylbenzene (DIPB) of the catalyst was determined by calculating the ratio of DIPB to cumene (isopropylbenzene) production. Thus, a lower selectivity to DIPB represents a more mono-selective catalyst composition.

Table 1 shows the alkylation activity and selectivity of Catalysts 1-7 based on the results.

TABLE 1

| | Relative Catalyst Activity | | | |
|---|---|---|---|---|
| Catalyst | Rate Constant (k) | Relative activity | % Di-Propyl-Benzene | Description |
| 1 | 237 | 1 | 17.9 | Reference |
| 2 | 245 | 1.03 | 31.3 | ≤2 wt % F (static exposure) |
| 3 | 348 | 1.47 | 31.6 | ≤2 wt % F |
| 4 | 361 | 1.52 | 31.9 | ≤1.6 wt % F |
| 5 | 399 | 1.68 | 30.0 | ≤1.2 wt % F |
| 6 | 359 | 1.51 | 28.5 | ≤0.8 wt % F |
| 7 | 335 | 1.41 | 23.6 | ≤0.4 wt % F |

As shown in Table 1, Catalyst 1 is used as a reference, so the rate constant "k" for Catalyst 1 is used to normalize the activity for the other catalysts. Catalysts 3-7 all show a substantial increase in alkylation activity as indicated by the normalized reaction constant values. Catalysts 3-7 also show a substantial increase in the amount of dialkylation that occurred during the reaction. The percentage of dialkylation represents the percentage of alkylated aromatics that corresponded to dipropylbenzene as opposed to propylbenzene. It is noted that catalysts similar to Catalysts 3-7 but with still higher amounts of fluorine were also prepared. It was found that further increases in the amount of fluorine resulted in similar activity to Catalyst 3 or lower. Catalyst 2, which was formed without mixing during exposure of the MCM-49 crystals to the molten $SnF_2$, showed an increase in dialkyl formation that is similar to Catalysts 3-7, but with a reaction constant k that was substantially the same as reference Catalyst 1 (not fluorinated).

Figure 1:
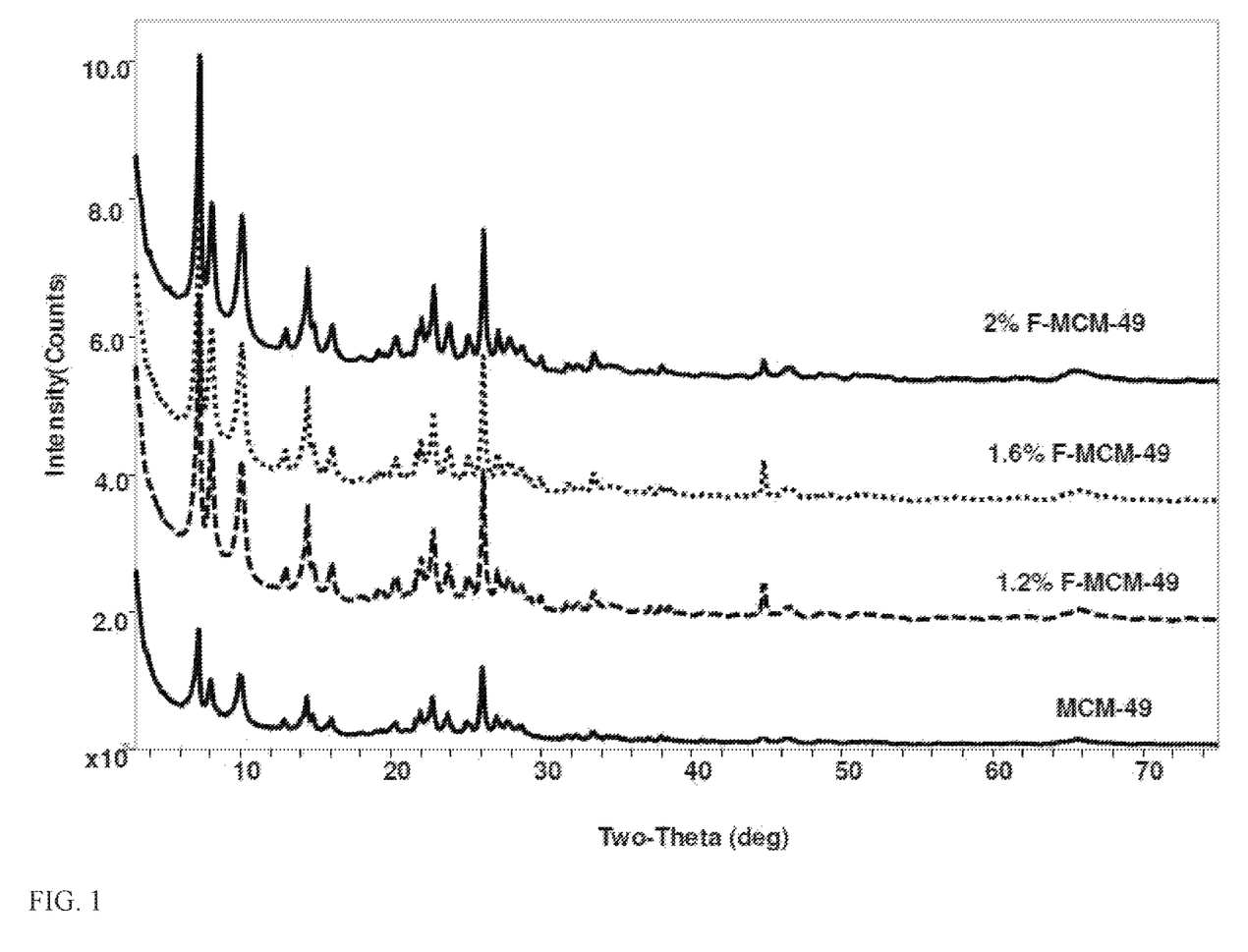
FIG. 1 shows X-ray diffraction data for fluorinated MCM-49 crystals produced by exposing MCM-49 crystals to molten $SnF_2$.

Based on Table 1, Catalysts 3-7 showed a substantial activity advantage over the non-fluorinated reference Catalyst 1. This demonstrates the ability of a molten metal fluoride to improve the alkylation activity of a zeolitic catalyst. FIG. 1 shows that the molten metal fluoride treatment did not substantially alter the nature of the crystalline framework structure of the MCM-49. In FIG. 1, X-ray diffraction (XRD) plots are shown for Catalyst 3 (bottom plot), Catalyst 4 (middle plot), and Catalyst 5 (top plot). The plots for Catalysts 3, 4, and 5 are offset for ease of viewing. FIG. 1 also shows an additional offset X-ray diffraction plot for MCM-49 without fluorination. As shown in FIG. 1, Catalysts 3, 4, and 5 each appear to have the peaks corresponding to the X-ray diffraction pattern for MCM-49.

Figure 3:
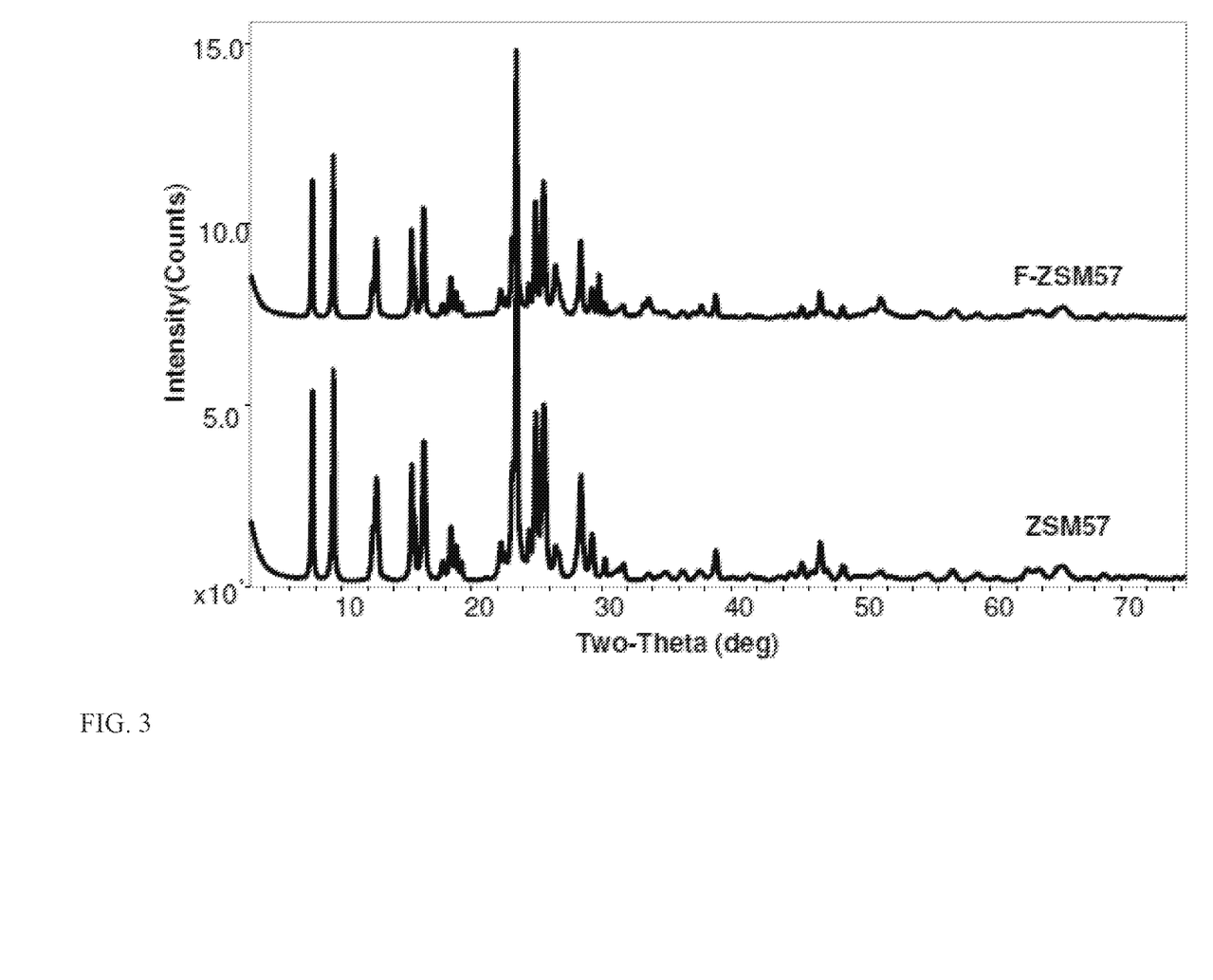
FIG. 3 shows X-ray diffraction data for fluorinated ZSM-57 crystals produced by exposing ZSM-57 crystals to molten $SnF_2$.

As another example of a zeolite retaining the crystalline framework without substantial alteration after a molten metal fluoride treatment, FIG. 3 shows XRD plots of ZSM-57 crystals before and after exposure of the crystals to molten $SnF_2$. As shown in FIG. 3, the fluorinated ZSM-57 crystals appear to have the peaks corresponding to the XRD pattern for ZSM-57.

In addition to X-ray diffraction, the surface area of the silica-bound fluorinated catalyst particles was also only modestly different relative to the silica-bound non-fluorinated catalyst precursor particles. The surface area of the MCM-49 crystals for Catalysts 1, 3, 4, and 5 was investigated by determining a BET ($N_2$) isotherm for each catalyst. The surface area of the extrudate particles for Catalyst 1 was roughly 492 $m^2/g$. The treatment of the MCM-49 crystals with molten metal fluoride appeared to cause a modest reduction in surface area for the resulting extrudate particles based on the fluorinated MCM-49 crystals. For Catalyst 5, the BET surface area of the extrudate particles was roughly 435 m²/g. For Catalyst 4, the BET surface area of the extrudate particles was roughly 439 m²/g. For Catalyst 3, the BET surface area of the extrudate particles was roughly 420 m²/g. The surface areas for the extrudate particles for each of Catalysts 3-5 were within 20% of the surface area of Catalyst 1, relative to the surface area of the extrudate particles for Catalyst 1. This is believed to demonstrate that the fluorinated MCM-49 crystals substantially retained the pore structure and pore volume present in the non-fluorinated MCM-49 crystals.

Figure 2:
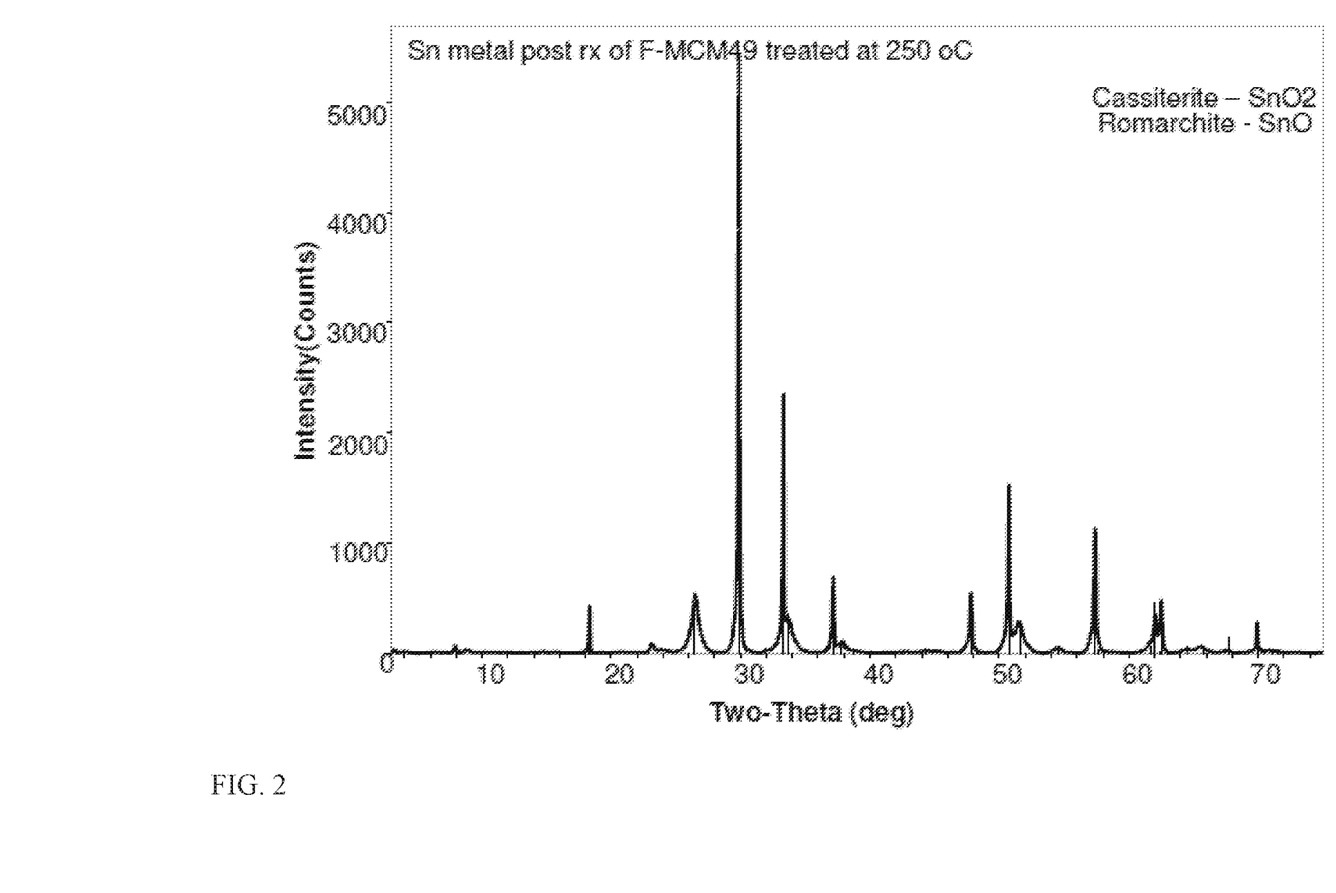
FIG. 2 shows X-ray diffraction data of tin oxide generated during exposure of MCM-49 crystals to molten $SnF_2$.

For Catalysts 3-7, it was also noted that a portion of a separate type of dense black powder could also be recovered after extrusion of the molten metal fluoride treated MCM-49 crystals. After extrusion, the reaction product from Catalysts 3-7 was sieved to allow for separation of the separate type of powder. The separate powder was characterized using X-ray diffraction to determine that the dense black powder was substantially composed of tin oxide. This is believed to demonstrate that a substantial portion of the tin from the molten $SnF_2$ was not incorporated into the framework structure. Instead, a separate tin oxide phase was formed. FIG. 2 shows the XRD plot of the separate tin oxide phase that was recovered from molten $SnF_2$ treatment of a sample of MCM-49 crystals. As indicated in FIG. 2, the peaks in the XRD plot are believed to indicate the presence of both SnO and $SnO_2$ in the tin oxide phase.

X-ray fluorescence (XRF) was used to further characterize the amount of Sn and F in the fluorinated MCM-49 crystals. It is noted that the error bounds for XRF can be as much as 0.5 wt %, which is substantial relative to the target fluorination amounts of 0.4 wt % to 2.0 wt %. However, the XRF data is believed to be sufficient to roughly provide confirmation that the target amounts of fluorine were incorporated into the zeolitic framework structure. Additionally, XRF was used to roughly determine the amount of Sn incorporated into the framework structure.

Fluorine and tin incorporation into the framework structure was characterized based on XRF of Catalyst 5. The initial amount of $SnF_2$ used for formation of Catalyst 5 corresponded to a maximum possibly fluorine concentration of roughly 1.2 wt %. Two XRF analysis runs of Catalyst 5 showed fluorine concentrations of about 1.01 and about 1.05 wt %. Based on the inherent uncertainty in XRF measurements, this is believed to indicate substantially complete incorporation of fluorine into the zeolitic framework structure. The XRF analysis also showed a tin concentration of 1.41 wt %. This is comparable to the amount of fluorine incorporated into the zeolitic framework structure, and therefore substantially less than the weight of tin present during the molten $SnF_2$ treatment. This is consistent with the presence of the separate tin oxide phase noted above.

The tin contents of Catalysts 3, 4, 6 and 7 were also determined using XRF. The tin contents are shown in Table 2. As shown in Table 2, the amount of tin incorporation into the zeolitic framework structure was generally comparable to the intended amount of fluorine incorporation for each of Catalysts 3, 4, and 7. The amount of tin incorporation was somewhat higher for Catalyst 6, although the additional tin incorporation (if any) is not believed to have impacted the activity of Catalyst 6 for alkylation.

TABLE 2

| Tin and Fluorine Content | | |
|---|---|---|
| Catalyst | Sn content (wt %) | F content (wt %) |
| 3 | 1.12; 1.13 | |
| 4 | 1.44; 1.49 | |
| 5 | 1.41; 1.41 | 1.01; 1.05 |
| 6 | 1.81; 2.05 | |
| 7 | 0.24; 0.26 | |

Additional Embodiments

Embodiment 1. A catalyst composition comprising an MWW framework structure, 0.1 wt % to 2.5 wt % fluorine relative to a weight of the catalyst composition, and a weight ratio of Sn to F in the catalyst composition of 0.1 to 2.0, or 0.1 to 1.5, the MWW framework structure optionally comprising a silicon to aluminum ratio of 2 to 100.

Embodiment 2. The catalyst composition of Embodiment 1, wherein the catalyst composition comprises a weight ratio of Sn to F in the MWW framework structure of 2.0 or less, or 1.5 or less, or 1.0 or less; or wherein the catalyst composition comprises a weight ratio of Sn to F in the MWW framework structure of 0.1 to 2.0, or 0.1 to 1.5, or 0.1 to 1.0.

Embodiment 3. The catalyst composition of any of the above embodiments, wherein the catalyst composition comprises MCM-49, MCM-22, MCM-56, or a combination thereof.

Embodiment 4. The catalyst composition of any of the above embodiments, wherein at least one of the MWW framework structure and the catalyst composition comprises 2.5 wt % or less Sn (or 0.01 wt % to 2.5 wt % Sn); or wherein the MWW framework structure comprises 0.1 wt % to 2.5 wt % fluorine; or a combination thereof.

Embodiment 5. The catalyst composition of any of the above embodiments, wherein the catalyst composition further comprises a binder.

Embodiment 6. A method for making an alkylation catalyst, comprising: exposing a catalyst precursor comprising a zeolitic framework structure to a molten metal salt comprising fluoride anion at a temperature of 275° C. or less; and mixing the catalyst precursor and the molten metal salt during at least a portion of the exposing to form a catalyst comprising a fluorinated zeolitic framework structure.

Embodiment 7. The method of claim 6, wherein the catalyst precursor comprises a MWW framework structure, a FAU framework structure, a MOR framework structure, a MEI framework structure, a MFS framework structure, a *BEA framework structure, a EMT-FAU structural intermediate framework structure, or a combination thereof, the MWW framework structure optionally comprising MCM-49, MCM-22, MCM-56, or a combination thereof.

Embodiment 8. The method of any of Embodiments 6 to 7, wherein the fluorinated zeolitic framework structure comprises 0.1 wt % fluorine or more, or 0.1 wt % to 2.5 wt % fluorine.

Embodiment 9. The method of any of Embodiments 6 to 8, wherein the molten metal salt comprises $SnF_2$, a molten metal fluoride, $TaF_5$, or a combination thereof.

Embodiment 10. The method of Embodiment 9, wherein the fluorinated zeolitic framework structure comprises 2.5 wt % or less Sn (or 0.01 wt % to 2.5 wt % Sn); or wherein a weight ratio of Sn to F in the fluorinated zeolitic framework structure is 2.0 or less, or 1.5 or less, or 1.0 or less; or a combination thereof.

Embodiment 11. The method of Embodiment 9 or 10, further comprising extruding at least a portion of the catalyst comprising a fluorinated zeolitic framework structure to form a catalyst composition, wherein a) the catalyst composition comprises 0.01 wt % to 2.5 wt % Sn; b) the catalyst composition comprises a weight ratio of Sn to F in the fluorinated zeolitic framework structure of 2.0 or less, or 1.5 or less, or 1.0 or less; c) the catalyst composition comprises 0.1 wt % to 2.5 wt % fluorine; or d) a combination of two or more of a), b), and c).

Embodiment 12. The method of any of Embodiments 6 to 11, wherein the catalyst composition further comprises a binder.

Embodiment 13. The method of Embodiment 12, wherein a surface area of the catalyst composition is different from a surface area of a catalyst precursor composition formed under substantially similar extruding and calcining conditions by 25% or less relative to the surface area of the catalyst precursor composition, or 20% or less, or 15% or less.

Embodiment 14. A method for performing alkylation, comprising: exposing a feedstock to a catalyst under effective alkylation conditions to form an alkylated effluent composition, wherein a) the catalyst comprises a catalyst composition according to any of Embodiments 1 to 5 or a catalyst made according to the method of any of Embodiments 6 to 13 and/or b) wherein the catalyst comprises an MWW framework structure, 0.1 wt % to 2.5 wt % fluorine relative to a weight of the catalyst composition, and a weight ratio of Sn to F in the catalyst composition of 0.1 to 1.5.

Embodiment 15. The method of Embodiment 14, wherein the feedstock comprises olefinic hydrocarbons and 1-ring aromatic hydrocarbons, the 1-ring aromatic hydrocarbons optionally comprising benzene, or wherein the effective alkylation conditions comprise effective transalkylation conditions, the feedstock comprising alkylated aromatics.

While the present invention has been described and illustrated with respect to certain aspects, it is to be understood that the invention is not limited to the particulars disclosed and extends to all equivalents within the scope of the claims. Unless otherwise stated, all percentages, parts, ratios, etc. are by weight. Unless otherwise stated, a reference to a compound or component includes the compound or component by itself as well as in combination with other elements, compounds, or components, such as mixtures of compounds. Further, when an amount, concentration, or other value or parameter is given as a list of upper preferable values and lower preferable values, this is to be understood as specifically disclosing all ranges formed form any pair of an upper preferred value and a lower preferred value, regardless of whether ranges are separately disclosed. All patents, test procedures, and other documents cited herein, including priority documents, are fully incorporated by reference to the extent such disclosure is not inconsistent and for all jurisdictions in which such incorporation is permitted.

The invention claimed is:

1. A catalyst composition comprising an MWW framework structure, tin and fluorine, wherein the catalyst comprises 0.1 wt % to 2.5 wt % fluorine relative to a weight of the catalyst composition, and a weight ratio of Sn to F in the catalyst composition of 0.1 to 2.0.

2. The catalyst composition of claim 1, wherein the catalyst composition comprises MCM-49, MCM-22, MCM-56, or a combination thereof.

3. The catalyst composition of claim 1, wherein the MWW framework structure comprises a silicon to aluminum ratio of 2 to 100.

4. The catalyst composition of claim 1, wherein at least one of the MWW framework structure and the catalyst composition comprises 2.5 wt % or less Sn.

5. The catalyst composition of claim 1, wherein the catalyst composition further comprises a binder.

* * * * *